United States Patent [19]
Konwitz et al.

[11] Patent Number: 5,449,354
[45] Date of Patent: Sep. 12, 1995

[54] DEVICE FOR TREATING THE INTERIOR OF BODY CAVITIES WITH LASER ENERGY

[75] Inventors: Ellie Konwitz, Ramat Gan, Israel; Jacques Donnez, Brussels, Belgium

[73] Assignee: Laser Industries Ltd, Tel-Aviv, Israel

[21] Appl. No.: 162,926

[22] Filed: Dec. 8, 1993

[30] Foreign Application Priority Data

Dec. 15, 1992 [IL] Israel ..................................... 104100

[51] Int. Cl.⁶ ............................................. A61B 17/36
[52] U.S. Cl. ......................................... 606/15; 606/13; 607/89
[58] Field of Search ................... 606/7, 13, 16; 607/89

[56] References Cited

U.S. PATENT DOCUMENTS

| | | | |
|---|---|---|---|
| 4,313,431 | 2/1982 | Frank | 606/16 |
| 4,799,479 | 1/1989 | Spears | 606/7 |
| 4,998,930 | 3/1991 | Lundahl | 606/15 |
| 5,156,604 | 10/1992 | Hessel et al. | 606/16 |
| 5,188,634 | 2/1993 | Hussein et al. | 606/7 |

Primary Examiner—Stephen C. Pellegrino
Assistant Examiner—Michael Peffley
Attorney, Agent, or Firm—Benjamin J. Barish

[57] ABSTRACT

A device for treating the interior of a body cavity with laser energy includes a cannula having a distal end adapted to be inserted into the body cavity to be treated, and a proximal end to be located externally of the body cavity when the distal end is inserted therein, and an optical fiber axially movable within the cannula to either a retracted, non-operative position or to an extended, operative position. The optical fiber has a proximal end to be coupled to a source of laser energy, and a distal end to project outwardly of the cannula in the extended, operative position of the optical fiber. The distal end of the optical fiber has a roughened outer surface for scattering the laser energy laterally outwardly of the optical fiber.

19 Claims, 3 Drawing Sheets

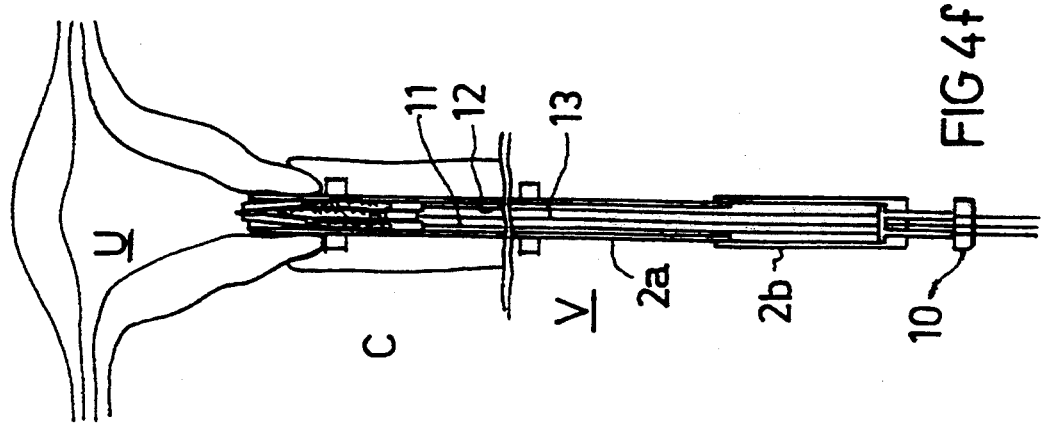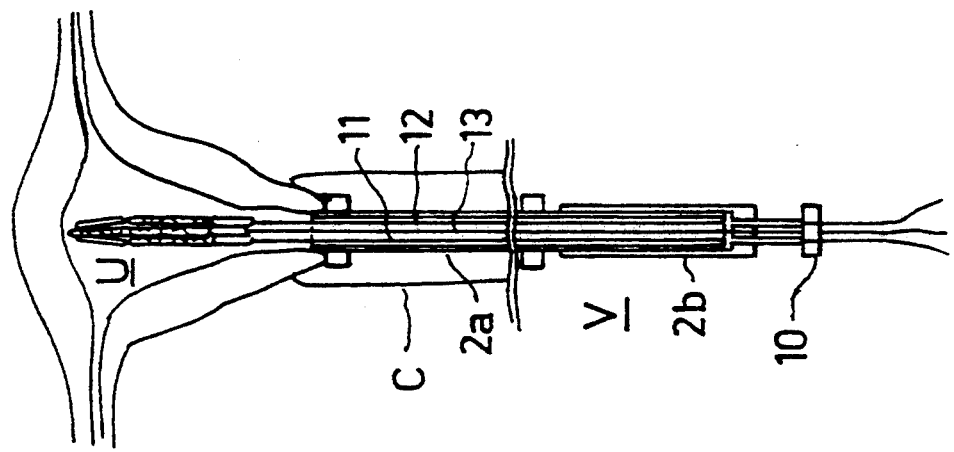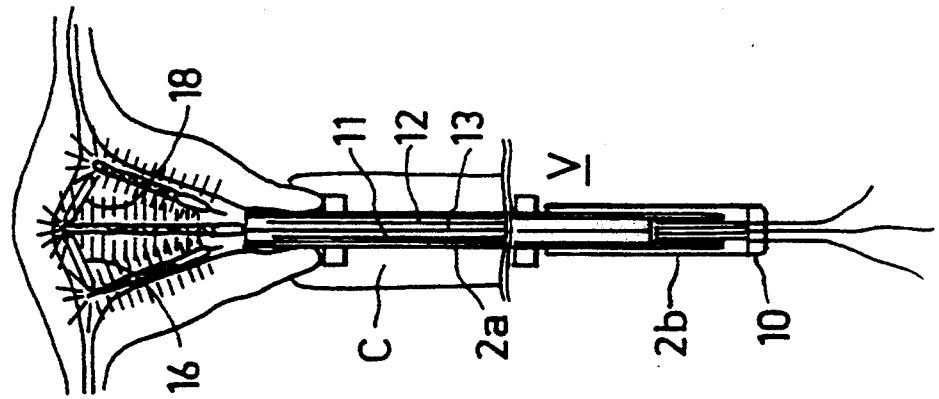

DEVICE FOR TREATING THE INTERIOR OF BODY CAVITIES WITH LASER ENERGY

FIELD AND BACKGROUND OF THE INVENTION

The present invention relates to a device for treating the interior of a body cavity with laser energy. The invention is particularly useful for the treatment of chronic menorrhagia, and is therefore described below with respect to such an application, but it will be appreciated that the invention conceivably could be used in other applications as well.

Chronic menorrhagia, defined as excessive and/or prolonged menstrual bleeding, is commonly treated by birth control pills, other hormonal therapies, or by a minor operation called "D and C" (dilation and curettage) involving a scraping of the lining of the uterus. When such treatments are not effective, a hysterectomy is generally performed involving removing the uterus and the lining along with it. Approximately 600,000 hysterectomies are performed in the USA each year.

Recently, a technique has been developed using laser energy to burn the uterine lining such as to cause scarring that prevents the lining from growing back. In this technique, a laser beam is conducted into the uterus by means of an optical fiber. The optical fiber is inserted via a channel of a hysteroscope, enabling the physician to view the interior of the uterus as he manipulates the tip of the optical fiber. He sweeps the tip of the optical fiber across the uterine lining to ablate the lining to a depth of about 3-5 mm. This procedure is generally quite painful because of the need to insert the hysteroscope and to dilate the uterus, usually done with a liquid, to enable the physician to view all the surfaces of the uterine lining as he manipulates the tip of the optical fiber over the uterine lining.

OBJECTS AND BRIEF SUMMARY OF THE INVENTION

An object of the present invention is to provide a device for treating the interior of a body cavity with laser energy, and particularly to a device useful for treating chronic menorrhagia with laser energy in order to ablate or coagulate the uterine lining.

According to the present invention, there is provided a device for treating the interior of a body cavity with laser energy, comprising: a first optical fiber having a distal end to be inserted into the body cavity to be treated, and a proximal end to be located externally of the body cavity when the distal end is inserted therein and to be coupled to a source of laser energy; and a second optical fiber axially movable with respect to the first optical fiber to either a retracted, non-operative position or to an extended, operative position. The second optical fiber includes a proximal end to be located externally of the body cavity and to be coupled to a source of laser energy, and a distal end to be inserted into the body cavity with the first optical fiber and mechanically coupled to the distal end of the first optical fiber such that the movement of the second optical fiber axially with respect to the first optical fiber causes the distal ends of both optical fibers to move in the lateral direction. The distal ends of the optical fibers have means for directing the laser energy outwardly of the optical fibers.

According to further features in the preferred embodiment of the invention described below, the device includes at least two, and preferably three, of said optical fibers within the cannula. When three optical fibers are included, they are arranged in a side-by-side relation, with the two outer fibers being axially movable with respect to the middle fiber, such that when the two outer fibers are so moved, the distal ends of all three fibers are spread apart laterally.

Such a laser device is particularly useful for treating chronic menorrhagia since a single dosage of laser energy will substantially cover most or all of the uterine lining. Thus, the device avoids the need for the physician to view the interior of the uterus, and thereby the need for inserting a hysteroscope into the uterus. It reduces, or perhaps may even eliminate, the dilation required of the uterus, and also substantially reduces the time of treatment.

Further features and advantages of the invention will be apparent from the description below.

BRIEF DESCRIPTION OF THE DRAWINGS

The invention is herein described, by way of example only, with reference to the accompanying drawings, wherein:

and FIGS. 4a-4f illustrate the use of the device of FIGS. 1 and 2 in treating chronic menorrhagia.

DESCRIPTION OF A PREFERRED EMBODIMENT

Figure 2:
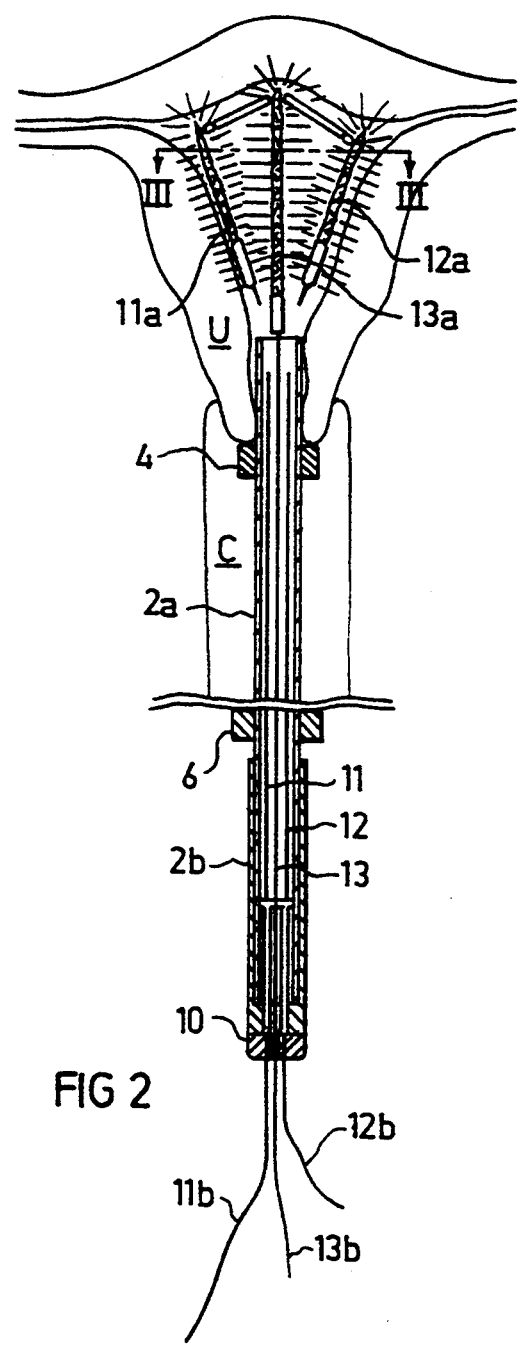
FIG. 2 is a view of the device of FIG. 1 in its operative condition.

The device illustrated in the drawings comprises a cannula, generally designed 2, constituted of two telescoping sections, namely an outer or distal section 2a, and an inner or proximal section 2b. When the device is used for treating chronic menorrhagia, as shown in FIGS. 4a-4f, the distal section 2a of the cannula is inserted via the patient's vagina V and cervix C into the uterus U; whereas the outer end of the proximal section 2b of the cannula is disposed externally of the patient's vagina. The two telescoping section 2a, 2b of the cannula are flattened to correspond to the flattened shape of the vagina as shown in FIG. 2. A ring 4 fixed to the distal end of cannula section 2a limits against the mouth of the uterus U during use of the device, and another ring 6 fixed to a mid-portion of cannula section 2a limits against the mouth of the cervix C. The distal end of cannula section 2a is open, whereas the proximal end of cannula section 2b is closed by an end wall 8 penetrated by a plunger 10 movable within cannula section 2b.

Three optical fibers 11, 12 and 13, are disposed in side-by-side relation within cannula 2. Each optical fiber includes a distal end 11a, 12a, 13a, to be located within the uterus during use of the device, and a proximal end 11b, 12b, 13b, to be located externally of the patient's body and to be coupled to a source of laser energy. The two outer optical fibers 11, 12 are axially movable with respect to the middle optical fiber 13. For this purpose, the proximal ends of the two outer fibers 11, 12 are fixed to the plunger 10, whereas the middle fiber 13 passes through a bore 10a in plunger 10 so that movement of the plunger into cannula section 2b will move the two outer fibers 11, 12 axially with respect to the middle fiber 13. The middle fiber 13, however, is fixed to the end wall 8 of cannula section 2b so that cannula section 2b may be moved, together with plunger 10, to move all three optical fibers axially within the cannula.

The distal ends 11a, 12a, 13, of the three optical fibers are toughened on their outer surfaces so that the laser energy, applied to the proximal ends 11b, 12b, 13b, of the three optical fibers, is conducted through their respective fibers and is scattered laterally outwardly of the optical fibers at their distal ends.

As shown particularly in FIG. 2, the distal ends 11a, 12a, 13a, of the three optical fibers are coupled together such that the movement of the two outer optical fibers 11, 12, axially with respect to the middle fiber 13, causes the distal ends of the three optical fibers to spread apart laterally. For this purpose, the distal ends of the outer fiber 11 and the middle fiber 13 are coupled together by a rod 16 pivotally mounted at its opposite ends to the two fibers; similarly, the distal ends of the outer fiber 12 and middle fiber 13 are coupled together by a second rod 18 pivotally mounted at its opposite ends to the two fibers.

Preferably, the roughened distal ends 11a, 12a, 13a of the three optical fibers are each covered by an outer glass or quartz tube to avoid carbonization thereon. In addition, the rods 16, 18 are preferably of metal.

FIGS. 4a-4f illustrate one manner of using the above-described device for treating chronic menorrhagia.

Figure 1:
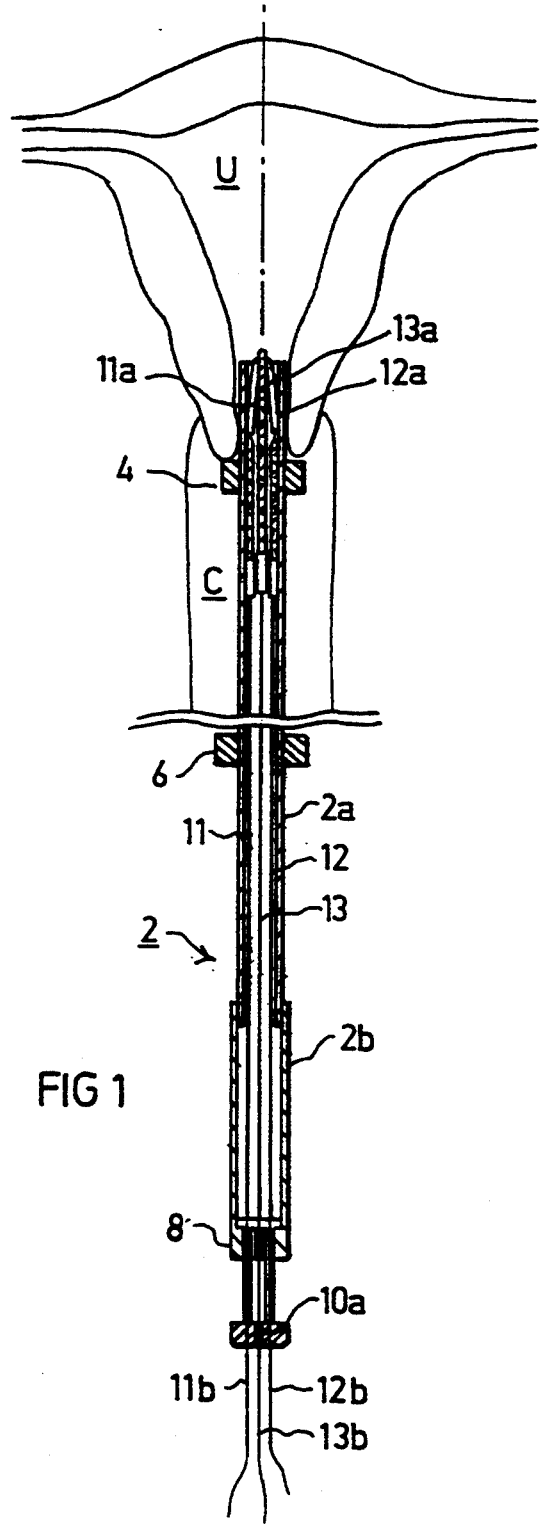
FIG. 1 illustrates one form of device constructed in accordance with the present invention, the device being shown in its initial, non-operative condition.
Figure 4C:
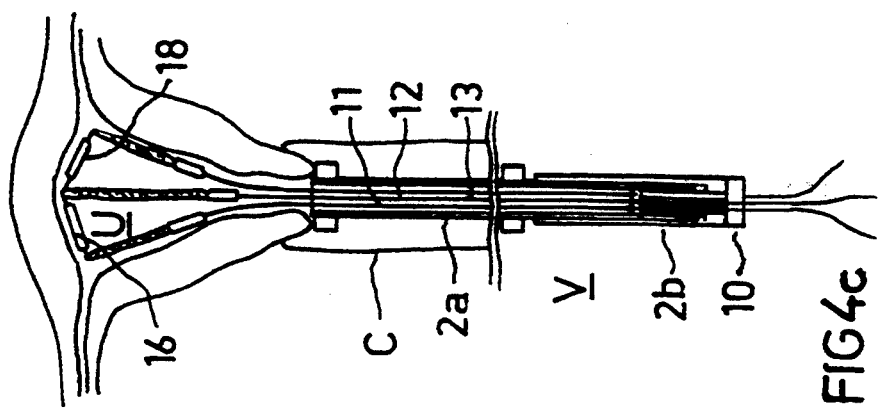
Figure 4B:
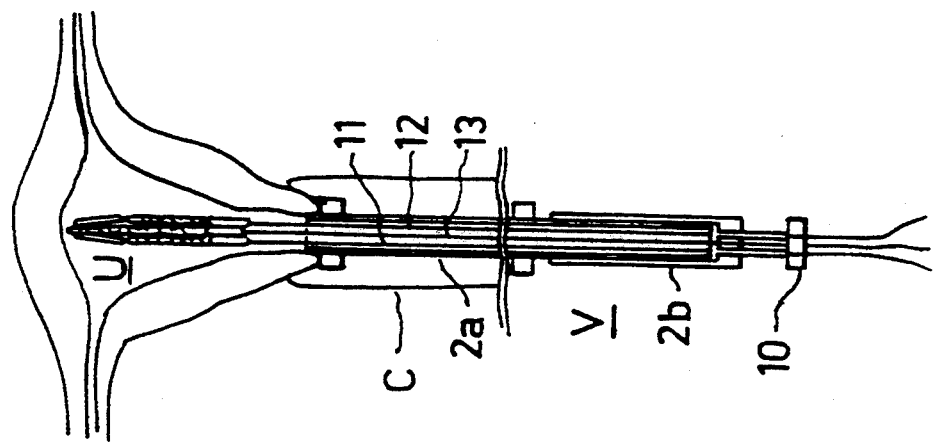
Figure 4A:
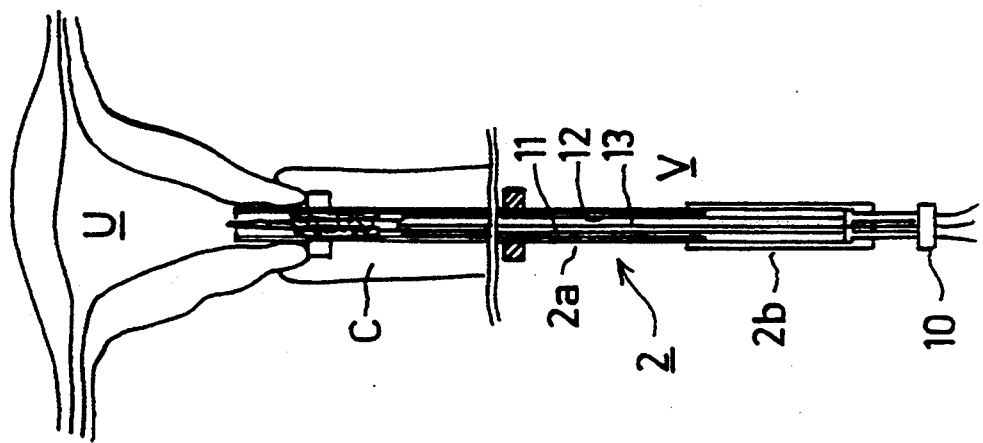

Initially, the illustrated device is in the condition illustrated in FIG. 4a (also in FIG. 1), wherein cannula section 2b is moved outwardly so as to move all three optical fibers 11, 12, 13, to their retracted, non-operative positions, wherein the fibers, and particularly their distal ends, are completely enclosed by the cannula 2. In this initial position, the plunger 10 is also in its outer position, such that the distal tips of the two outer fibers 11, 12, are behind the distal tip of the inner fiber 13, whereby the two rods 16, 18 at the distal tips of the three fibers cause the distal tips to assume a substantially parallel, side-by-side relation to each other.

The cannula is then inserted through the patient-'vagina V and cervix C to the position illustrated in FIG. 4a, wherein ring 4 abuts against the mouth of the uterus U, ring 6 abuts against the mouth of the cervix C, and a portion of the proximal cannula sectin 2b extending externally of the patient'vagina. Cannula section 2b is then moved axially with respect to cannula section 2a to the position illustrated in FIG. 4b. This causes the distal ends of the three optical fibers 11a, 12a, 13a, to move into the patient's uterus U as shown in FIG. 4b. Plunger 10 is then moved axially with respect to cannula section 2b, which causes the two outer optical fibers 11, 12, to move axially with respect to the middle fiber 13, as shown in FIG. 4c (and also in FIG. 2). During this movement of the two outer fibers 11, 12, the rods 16, 18, connecting their distal ends to the middle fiber 13, cause the distal ends of the outer fibers to spread laterally with respect to the middle fiber.

Figure 3:
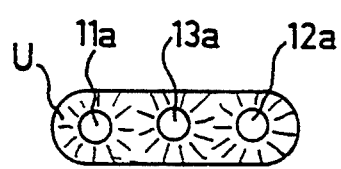
FIG. 3 is a cross-sectional view along line III—III of FIG. 2.

When the device is in this condition, laser energy is applied for a predetermined time period to the proximal ends of the three optical fibers 11, 12, 13. This laser energy is transmitted through each of the fibers to their respective distal ends 11a, 12a, 13a, and is scattered laterally outwardly of the optical fibers by the roughened surfaces at these distal ends. Since the uterus U is relatively flat as shown in FIG. 3, substantially the complete uterine lining is thus exposed to the laser energy without the need to rotate or otherwise manipulate the optical fibers in order to cover the complete surface of the uterine lining.

After this exposure of the uterine lining to the laser energy, the cannula 2 is pulled out about 1.5 cm out of the cervix C (FIG. 4d); the plunger 10 is then withdrawn from cannula section 2b to thereby pivot the distal ends 11a, 12a, of the two outer fibers back to their side-by-side positions with respect to the distal end 13a of the middle fiber (FIG. 4e); and then cannula section 2b is moved outwardly with respect to cannula section 2a (FIG. 4f) to thereby move all three fibers to their retracted, non-operative positions, with respect to the cannula. The cannula then may be withdrawn.

For purposes of example, the roughened distal ends 11a, 12a, 13a, of the three optical fibers may be for a length of 30 mm; the laser energy applied may be that from a Nd-YAG laser; 10 watts may be applied to each optical fiber; and the exposure may be for a duration of about five minutes. Such a treatment causes ablation of the uterine lining to a depth of about 5 mm, which normally would be sufficient to prevent the uterine lining from growing back.

While the invention has been described with respect to one preferred embodiment, it will be appreciated that many variations, modifications and other applications of the invention may be made.

What is claimed is:

1. A device for treating the interior of a body cavity with laser energy, comprising:
    a first optical fiber having a distal end adapted to be inserted into the body cavity to be treated, and a proximal end to be located externally of the body cavity when the distal end is inserted therein and to be coupled to a source of laser energy;
    a second optical fiber axially movable with respect to said first optical fiber to either a retracted, non-operative position or to an extended, operative position;
    said second optical fiber including a proximal end to be located externally of the body cavity and to be coupled to a source of laser energy, and a distal end to be inserted into the body cavity with said first optical fiber and mechanically coupled to the distal end of said first optical fiber such that the movement of said second optical fiber axially with respect to said first optical fiber causes the distal ends of both optical fibers to move in the lateral direction;
    said distal ends of the optical fibers having means for directing the laser energy outwardly of the optical fibers.

2. The device according to claim 1, wherein the distal ends of the two optical fibers are mechanically coupled together by a rod pivotally mounted at one end to one of the optical fibers, and at its opposite end to the other optical fiber.

3. The device according to claim 1, wherein said optical fibers are movable within a cannula which includes:
    a distal section insertable into the body cavity;
    and a proximal section telescopingly movable with respect to said distal section;
    both said fibers being fixed to said proximal section of the cannula to enable both fibers to be moved axially together with respect to the distal section of the cannula to either said retracted, non-operative position or projected, operative position.

4. The device according to claim 3, further including a plunger receivable within and movable inwardly of said proximal section of the cannula;

said plunger being fixed to one of said optical fibers but being freely movable with respect to the other optical fiber such that movement of the plunger inwardly of the proximal section of the cannula causes said one optical fiber to move axially with respect to said other optical fiber.

5. The device according to claim 1, wherein there are at least three optical fibers arranged in a side-by-side relation, with two of the fibers being outer fibers, and the third fiber being the middle fiber straddled on opposite sides by the two outer fibers;

the two outer fibers being axially movable with respect to the middle fiber;

the distal ends of the three fibers being mechanically coupled together such that movement of the two outer fibers axially with respect to the middle fiber causes the distal ends of all three fibers to spread apart laterally.

6. The device according to claim 5, wherein the distal ends of the two outer optical fibers are each mechanically coupled to the middle optical fiber by a rod pivotally mounted at one end to the respective outer optical fiber, and at its opposite end to the middle optical fiber.

7. The device according to claim 5, wherein said optical fibers are movable within a cannula which includes:

a distal section insertable into the body cavity;

and a proximal section telescopingly movable with respect to said distal section;

all of said optical fibers being fixed to said proximal section of the cannula to enable all the fibers to be moved axially together to their retracted, non-operative positions or to their projected, operative positions with respect to the distal section of the cannula.

8. The device according to claim 7, further including a plunger receivable within and movable inwardly of the proximal section of the cannula;

said plunger being fixed to the two outer optical fibers but being freely movable with respect to the middle optical fiber such that movement of the plunger inwardly of the proximal section of the cannula causes said two outer optical fibers to move axially with respect to said middle optical fiber.

9. The device according to claim 1, wherein said directing means comprises a roughened outer surface formed on the distal end of each of said optical fibers for scattering the laser energy laterally outwardly of the optical fiber.

10. A device for treating the interior of a body cavity with laser energy, comprising:

at least two optical fibers each having a distal end adapted to be inserted into the body cavity to be treated, and a proximal end to be located externally of the body cavity when the distal end is inserted therein and to be coupled to a source of laser energy;

one of said optical fibers being axially movable with respect to the other optical fiber to either a retracted, non-operative position or to an extended, operative position;

the distal ends of the two optical fibers being mechanically coupled together such that movement of one optical fiber axially with respect to the other causes the distal ends of the two optical fibers to spread apart laterally;

said distal ends of the optical fibers directing the laser energy outwardly of the optical fiber.

11. The device according to claim 10, wherein said optical fibers are disposed within a cannula having a distal end adapted to be inserted into the body cavity to be treated, and a proximal end to be located externally of the body cavity when the distal end is inserted therein.

12. The device according to claim 1, wherein the distal ends of the two optical fibers are mechanically coupled together by a rod pivotally mounted at one end to one of the optical fibers, and at its opposite end to the other optical fiber.

13. The device according to claim 11, wherein said cannula includes:

a distal section insertable into the body cavity;

and a proximal section telescopingly movable with respect to said distal section;

both said fibers being fixed to said proximal section of the cannula to enable both fibers to be moved axially together with respect to the distal section of the cannula to either said retracted, non-operative position or projected, operative position.

14. The device according to claim 13, further including a plunger receivable within and movable inwardly of said proximal section of the cannula;

said plunger being fixed to one of said optical fibers but being freely movable with respect to the other optical fiber such that movement of the plunger inwardly of the proximal section of the cannula causes said one optical fiber to move axially with respect to said other optical fiber.

15. The device according to claim 10, wherein there are at least three optical fibers within said cannula arranged in a side-by-side relation, with two of the fibers being outer fibers, and the third fiber being the middle fiber straddled on opposite sides by the two outer fibers;

the two outer fibers being axially movable with respect to the middle fiber;

the distal ends of the three fibers being mechanically coupled together such that movement of the two outer fibers axially with respect to the middle fiber causes the distal ends of all three fibers to spread apart laterally.

16. The device according to claim 15, wherein the distal ends of the two outer optical fibers are each mechanically coupled to the middle optical fiber by a rod pivotally mounted at one end to the respective outer optical fiber, and at its opposite end to the middle optical fiber.

17. The device according to claim 15, wherein said optical fibers are movable within a cannula which includes:

a distal section insertable into the body cavity;

and a proximal section telescopingly movable with respect to said distal section;

all of said optical fibers being fixed to said proximal section of the cannula to enable all the fibers to be moved axially together to their retracted, non-operative positions or to their projected, operative positions with respect to the distal section of the cannula.

18. The device according to claim 17, further including a plunger receivable within and movable inwardly of the proximal section of the cannula;

said plunger being fixed to the two outer optical fibers but being freely movable with respect to the middle optical fiber such that movement of the plunger inwardly of the proximal section of the cannula causes said two outer optical fibers to move axially with respect to said middle optical fiber.

19. The device according to claim 10, wherein the distal end of each of said optical fibers is formed with a roughened outer surface for scattering energy laterally outwardly of the optical fibers.

* * * * *